US008722557B2

(12) United States Patent
Shum

(10) Patent No.: US 8,722,557 B2
(45) Date of Patent: May 13, 2014

(54) CATALYST REGENERATION

(75) Inventor: Wilfred Po-sum Shum, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 432 days.

(21) Appl. No.: 12/317,873

(22) Filed: Dec. 30, 2008

(65) Prior Publication Data

US 2010/0167911 A1    Jul. 1, 2010

(51) Int. Cl.
*B01J 38/16* (2006.01)

(52) U.S. Cl.
USPC .................................................. 502/51

(58) Field of Classification Search
None
See application file for complete search history.

(56) References Cited

U.S. PATENT DOCUMENTS

| | | | |
|---|---|---|---|
| 3,865,751 A | | 2/1975 | Banks et al. |
| 3,962,126 A | * | 6/1976 | Pecak ........................ 502/22 |
| 3,996,166 A | | 12/1976 | Banks et al. |
| 4,060,560 A | * | 11/1977 | Leach ........................ 568/805 |
| 4,217,244 A | | 8/1980 | Montgomery |
| 4,242,530 A | | 12/1980 | Smith, Jr. |
| 4,406,775 A | * | 9/1983 | Bailor et al. ............... 208/140 |
| 4,513,099 A | | 4/1985 | Kukes et al. |
| 4,559,320 A | | 12/1985 | Reusser |
| 4,567,159 A | | 1/1986 | Banks et al. |
| 4,605,810 A | | 8/1986 | Banks |
| 4,644,086 A | * | 2/1987 | Voges et al. ................ 568/804 |
| 4,769,501 A | * | 9/1988 | Iwahara ...................... 568/799 |
| 5,120,894 A | | 6/1992 | McCauley |
| 5,134,103 A | | 7/1992 | Lowery et al. |
| 5,300,718 A | * | 4/1994 | McCaulley ................ 585/324 |
| 6,586,649 B1 | | 7/2003 | Botha et al. |
| 6,875,901 B2 | | 4/2005 | Gartside et al. |
| 7,214,841 B2 | * | 5/2007 | Gartside et al. ............ 585/324 |
| 2003/0004385 A1 | | 1/2003 | Gartside et al. |
| 2005/0096492 A1 | * | 5/2005 | Dath et al. ................. 585/653 |
| 2007/0129235 A1 | | 6/2007 | Brown |
| 2008/0146856 A1 | | 6/2008 | Leyshon |
| 2008/0312481 A1 | * | 12/2008 | Leyshon ..................... 585/324 |
| 2009/0232939 A1 | | 9/2009 | Berge |
| 2010/0152022 A1 | | 6/2010 | Sun et al. |

FOREIGN PATENT DOCUMENTS

| | | |
|---|---|---|
| CN | 1098083 A | 2/1995 |
| JP | 2009524427 | 7/2009 |
| RU | 2140410 | 12/1994 |
| WO | WO94/08922 | 4/1994 |
| WO | WO 2008/088453 A2 | 7/2008 |
| WO | WO 2009/013964 A1 | 1/2009 |
| WO | WO2010/077262 | 7/2010 |

OTHER PUBLICATIONS

"Butylenes," *Kirk-Othmer Encyclopedia of Chemical Technology*, John Wiley & Sons, Inc., 2008, pp. 402-433.
Robert L. Banks, *Applied Industrial Catalysis*, vol. 3, 1984, Chapter 7, "Olefin Metathesis: Technology and Application," pp. 215-239.
Alvin B. Stiles, *Catalyst Manufacture Laboratory and Commercial Preparation*, Marcel Dekker, Inc., 1983, Chapter 6, "Calcining," pp. 51-57.
Chinese Office Action and Search Report Mailed Nov. 22, 2012 for Chinese Application No. 200980153568.4.
Russian Notice of Allowance Mailed Sep. 19, 2013 for Russian Application No. 2011132046/04(047232).

* cited by examiner

*Primary Examiner* — Melvin C Mayes
*Assistant Examiner* — Stefanie Cohen

(57) ABSTRACT

A method is disclosed for regenerating a used catalyst mixture comprising (i) an isomerization catalyst comprising magnesium oxide and (ii) a metathesis catalyst comprising an inorganic carrier and at least one of molybdenum oxide and tungsten oxide. The method comprises (a) decoking the used catalyst mixture in the presence of an oxygen-containing gas to produce a decoked catalyst mixture; and (b) contacting the decoked catalyst mixture with steam at a temperature in the range of 100 to 300° C. to produce a regenerated catalyst mixture.

9 Claims, No Drawings

CATALYST REGENERATION

FIELD OF THE INVENTION

The invention relates to a method of regenerating a catalyst mixture comprising an isomerization catalyst and a metathesis catalyst.

BACKGROUND OF THE INVENTION

Steam cracking of hydrocarbons is a petrochemical process that is widely used to produce olefins such as ethylene, propylene, $C_4$ olefins (1-butene, 2-butenes, isobutene), butadiene, and aromatics such as benzene, toluene, and xylene. 2-Butenes include cis-2-butene and/or trans-2-butene. In an olefin plant, a hydrocarbon feedstock such as naphtha, gas oil, or other fractions of whole crude oil is mixed with steam. This mixture, after preheating, is subjected to severe thermal cracking at elevated temperatures in a pyrolysis furnace. The cracked effluent from the pyrolysis furnace contains gaseous hydrocarbons of great variety (from 1 to 35 carbon atoms per molecule). This effluent contains hydrocarbons that are aliphatic, aromatic, saturated, and unsaturated, and may contain significant amounts of molecular hydrogen. The cracked product of a pyrolysis furnace is then further processed in the olefin plant to produce, as products of the plant, various individual product streams such as hydrogen, ethylene, propylene, mixed hydrocarbons having four or five carbon atoms per molecule, and pyrolysis gasoline.

Crude $C_4$ hydrocarbons can contain varying amounts of n-butane, isobutane, $C_4$ olefins, acetylenes (ethyl acetylene and vinyl acetylene), and butadiene. See *Kirk-Othmer Encyclopedia of Chemical Technology*, online edition (2008). Crude $C_4$ hydrocarbons are typically subjected to butadiene extraction or butadiene selective hydrogenation to remove most, if not essentially all, of the butadiene and acetylenes present. Thereafter the $C_4$ raffinate (called raffinate-1) is subjected to a chemical reaction (e.g., etherification, hydration, or dimerization) wherein the isobutene is converted to other compounds (e.g., methyl tert-butyl ether, tert-butyl alcohol, or diisobutene) (see, e.g., U.S. Pat. Nos. 6,586,649 and 4,242,530). The remaining $C_4$ stream containing mainly n-butane, isobutane, 1-butene and 2-butenes is called raffinate-2. Paraffins (n-butane and isobutane) can be separated from the linear butenes (1-butene and 2-butenes) by extractive distillation. Linear butenes can react with ethylene to produce propylene through double-bond isomerization and metathesis reactions (*Appl. Ind. Catal.* 3 (1984) 215). For example, a mixture of magnesium oxide and silica-supported tungsten oxide can be used for the above transformation to produce propylene.

In a commercial plant, the catalyst tends to deactivate with time, possibly due to the formation of coke in the catalyst pores and on the catalyst surface. Therefore, the catalyst needs to be regenerated periodically. U.S. Pat. No. 4,605,810 teaches a method for regenerating a mixed bed of magnesium oxide and $WO_3$-on-silica by flowing air at 600° C. followed by a nitrogen flush at 600° C. for about 15 minutes, optionally a carbon monoxide flow for at 600° C., and finally a nitrogen flush to cool the catalyst to the desired reaction temperature. However, the present inventor found that such a regeneration method cause significant loss of the catalyst strength, particularly the magnesium oxide.

Magnesium oxide itself is known to be useful as an olefin double-bond isomerization catalyst (see, e.g., U.S. Pat. Nos. 4,217,244 and 5,134,103).

Methods for regenerating MgO-containing catalysts are known. U.S. Pat. No. 3,962,126 teaches a method for reactivating a carbonized magnesium oxide catalyst that has become carbonized when it is in a phenol alkylation reaction, which comprises burning carbon from the catalyst by exposing the catalyst to heat in an oxygen containing gas, to form a partially reactivated catalyst, the improvement which consists essentially of contacting the partially reactivated catalyst with a sufficient amount of water at a temperature below 300° C. to restore the activity of the catalyst.

U.S. Pat. No. 4,217,244 describes a regeneration method of a olefin isomerization catalyst containing magnesium oxide. The regeneration involves purging the catalyst with an inert gas, and then treating the catalyst with an oxygen-containing gas at a temperature not to exceed about 1000° F. (538° C.).

U.S. Pat. No. 5,134,103 discloses a regeneration method of a spent magnesium oxide isomerization catalyst that involves calcining the catalyst at 425 to 590° C.

U.S. Pat. Appl. Pub. No. 2003/0004385 teaches decoking a deactivated magnesium oxide catalyst with a flowing gas containing a dry inert gas (e.g., nitrogen) and an oxidizing agent (e.g., oxygen) at a temperature of at least about 500° C. to substantially completely remove all coke from the catalyst. The regeneration is preferably carried out in steps of gradually increasing temperature and oxygen concentration.

SUMMARY OF THE INVENTION

The invention is a method for regenerating a used catalyst mixture comprising (i) an isomerization catalyst comprising magnesium oxide and (ii) a metathesis catalyst comprising an inorganic carrier and at least one of molybdenum oxide and tungsten oxide. The method comprises (a) decoking the used catalyst mixture in the presence of an oxygen-containing gas to produce a decoked catalyst mixture; and (b) contacting the decoked catalyst mixture with steam at a temperature in the range of 100 to 300° C. to produce a regenerated catalyst mixture.

DETAILED DESCRIPTION OF THE INVENTION

In the present disclosure, the catalyst is referred to as a fresh catalyst before it is used in a chemical process. After the catalyst is used in the process for a period of time and loses part of its original activity, the material is referred to as a used catalyst.

The invention is a method for regenerating a used catalyst mixture comprising (i) an isomerization catalyst comprising magnesium oxide and (ii) a metathesis catalyst comprising an inorganic carrier and at least one of molybdenum oxide and tungsten oxide, said method comprising: (a) decoking the used catalyst mixture in the presence of an oxygen-containing gas to produce a decoked catalyst mixture; and (b) contacting the decoked catalyst mixture with steam at a temperature in the range of 100 to 300° C. to produce a regenerated catalyst mixture. The catalyst mixture may be used to react ethylene with 1-butene and/or 2-butenes to produce propylene (U.S. Pat. No. 5,300,718).

The isomerization catalyst comprises magnesium oxide (magnesia). The isomerization catalyst can catalyze the double-bond isomerization of olefins, e.g., the conversion between 1-butene and 2-butenes. Many available magnesium oxides may be used as the isomerization catalyst. The isomerization catalyst may comprise other materials such as silica, alumina, titania, and the like. Preferably, the isomerization catalyst comprises primarily magnesium oxide, e.g., at least 95 weight percent (wt %) magnesium oxide, more preferably at least 98 wt % of magnesium oxide.

The metathesis catalyst comprises an inorganic carrier. Suitable inorganic carriers include alumina, silica, titania, magnesia-alumina, silica-alumina, titania-alumina, zirconia-alumina, alumina-titania-zirconia, thoria, aluminum phosphate, zirconium phosphate, calcium phosphate, magnesium phosphate, thorium phosphate, titanium phosphate, and the like. Preferred inorganic carriers comprise silica, preferably at least 90 wt % of silica, more preferably at least 99 wt % of silica. Generally, the inorganic carrier has a surface area of at least 10 m$^2$/g, preferably of 25 m$^2$/g to 800 m$^2$/g.

The metathesis catalyst comprises at least one of molybdenum oxide and tungsten oxide. The metathesis catalyst may be prepared by any convenient method including dry mixing, impregnation, ion-exchange, adsorption, and the like.

The oxide of molybdenum or tungsten is preferably combined with the inorganic carrier in a high positive oxidation state, e.g., hexavalent molybdenum or hexavalent tungsten. The proportion of the molybdenum or tungsten oxide combined with the inorganic carrier can vary, but generally the catalyst contains at least 0.1 wt % oxides of molybdenum and/or tungsten with amounts from about 0.2 wt % to about 30 wt % being preferred. More preferably, the metathesis catalyst contains 5 to 10 wt % oxides of molybdenum and/or tungsten.

The metathesis catalyst may comprise minor amounts alkali metals. Suitable alkali metals include lithium, sodium, potassium, rubidium, cesium and mixtures thereof. Sodium and potassium are preferred. The alkali metal may be present in the form of hydroxides, such as NaOH, KOH, and the like. The amount of alkali metal may be in the range of 100 ppm to 1 wt %, preferably from 1000 to 5000 ppm.

The isomerization and metathesis catalysts can be in any conventional shape, e.g., spheres, pellets, granules, extrudates, tablets, and the like. Preferably, their sizes are in the range of from 0.5 to 10 mm, more preferably from 1 to 5 mm. A fixed-bed reactor is preferably used. The reactor preferably is operated in a downflow fashion.

A mixture of the isomerization catalyst and the metathesis catalyst is used. The two catalysts may be blended before they are charged to a reactor. Alternatively, layers of each catalyst may be loaded in the reactor. For example, the catalyst bed may be configured so that the upstream end of the bed is substantially pure isomerization catalyst and the downstream end of the bed is a mixture of the isomerization catalyst and the metathesis catalyst. At the downstream end, the weight ratio of the two catalysts may range from about 2:8 to 8:2, usually from 6:4 to 4:6.

The overall weight ratio of the isomerization catalyst to the metathesis catalyst in the mixture can vary widely. Generally it is from 0.1:1 to 100:1, preferably from 0.5:1 to 20:1.

The reaction can be carried out at any convenient pressure, preferably 0 to 500 psig, typically 300 to 400 psig, and at weight hourly space velocities (WHSV) of about 0.01 to about 1,000 h$^{-1}$, usually in the range of 10 to 50 h$^{-1}$ based on the weight of the metathesis catalyst.

The catalyst mixture is used to produce olefins. The applicable feedstock include acyclic mono and polyenes having at least three carbon atoms per molecule and cycloalkyl and aryl derivatives thereof; cyclic mono and polyenes having at least four carbon atoms per molecule and alkyl and aryl derivatives thereof; mixtures of two or more of the above olefins; and mixtures of ethylene with one or more of the above olefins. Many useful reactions are accomplished with such acyclic olefins having 3 to 10 carbon atoms per molecule and with such cyclic olefins having 4 to 10 carbon atoms per molecule.

The preferred feedstock for the reaction comprises a linear olefin with at least four carbon atoms and ethylene. A particularly preferred feed stock is a mixture of a liner butene and ethylene. Propylene is produced from such a feedstock.

Before the feedstock is introduced to the reactor, the catalyst mixture may be activated in a suitable manner such as, for example, by heating in a flowing stream of an oxygen-containing gas for about 0.5 to 30 h at 250° C. to 600° C., preferably at 300° C. to 500° C. The catalyst mixture may be treated with a reducing gas such as carbon monoxide, hydrogen or a hydrocarbon at a temperature in the range of about 400 to about 700° C. to enhance its activity. Such reducing treatment is carried out preferably at 500 to 650° C. Such optional reducing treatment can suitably be carried out for a period of time ranging from about 1 min to about 30 h. After activation, it is sometimes advisable to flush the catalyst mixture with an inert gas to remove any adsorbed oxygen or other gases from the bed.

When the catalyst mixture is used in producing olefins, it tends to deactivate with time. Thus, it is necessary to regenerate the catalyst mixture from time to time.

This invention is a method for regenerating the catalyst mixture. The method comprises decoking the used catalyst mixture in the presence of an oxygen-containing gas to produce a decoked catalyst mixture. The oxygen concentration in the gas is not critical. It may be in the range of from 0.1 to 100 mole percent (mol %). Generally air or a mixture of oxygen and nitrogen is used. When necessary, a gas mixture containing low level of oxygen is used to reduce the exotherm during calcination and to prevent the so-called "hot spot" and the oxygen concentration is increased with time. In one preferred method, the used catalyst mixture is treated in an inert gas (e.g., nitrogen, argon, etc) to pyrolyze the organic material before it is calcined in an oxygen-containing gas.

The oxygen-containing gas may comprise steam. For example, it may comprise 5 to 90 mol % steam. Preferably it comprises 10 to 50 mol % steam.

Generally the decoking temperature is in the range of from 350 to 1000° C., more preferably from 450 to 800° C. The decoking step preferably takes place under conditions sufficient to assure relatively uniform temperature and uniform removal of coke and organic deposits.

The pressure at which the decoking is performed is not critical. Typically, it is carried out at atmospheric or slightly higher pressure.

The decoking step may be carried out in a stationary furnace, a fixed-bed reactor, a rotary kiln, or a belt calciner. See A. B. Stiles, Catalyst Manufacture, Marcel Dekker (1983), pp. 51-57. A rotary kiln is a cylindrical vessel, inclined slightly to the horizontal, which is rotated slowly about its axis. The material to be processed is fed into the upper end of the cylinder. As the kiln rotates, material gradually moves down towards the lower end, and undergoes a certain amount of mixing. Hot gases pass along the kiln, sometimes in the same direction as the catalyst (co-current), but usually in the opposite direction (counter-current). In a belt calciner, the catalyst may be loaded onto a belt where it is spread out in a uniformly thin layer. The catalyst then moves with the belt through a heating zone where the temperature and the composition of the atmosphere are controlled. Preferably, the catalyst mixture is decoked in the same reactor where the olefin-producing reaction is performed.

The decoked catalyst mixture generally contains less than 0.5 wt %, more preferably less than 0.1 wt % carbon.

The regeneration method comprises contacting the decoked catalyst mixture with steam at a temperature in the range of 100 to 300° C. to produce a regenerated catalyst mixture (steaming step). Preferably the steaming step is performed at a temperature in the range of 150 to 250° C. Generally, a mixture of a carrier gas and steam is used. Suitable carrier gases include nitrogen, air, and mixtures thereof. Nitrogen is a preferred carrier gas.

The amount of steam used relative to the carrier gas is not critical. Generally, the molar ratio of the steam to the carrier gas is 9:1 to 1:9.

EXAMPLE 1

Catalyst Deactivation

A reactor (¾ inch in outside diameter and 16 inch in length) is charged with 7.5 g fresh MgO cylindrical pellets (5 mm in diameter and 5 mm in length) at the top, and a blend of 22.5 g fresh MgO pellets and 7.5 g fresh $WO_3$/silica cylindrical pellets (5 mm in diameter and 5 mm in length) at the bottom. A feed gas containing 2-butenes and ethylene in a molar ratio of 1:1 is fed at the top of the reactor. The weight hourly space velocity of 2-butenes relative to $WO_3$/silica is 10 $h^{-1}$. Reaction temperature is increased to 500° C. and maintained at 500° C. The pressure is 5 psig. High reaction temperature is used to accelerate the catalyst deactivation. The catalyst bed loses greater than 50% of its activity in 30 h. The feed gas is stopped at 30 h.

Decoking of Deactivated Catalyst

The above reactor is depressurized to atmospheric pressure. The catalyst bed is purged with nitrogen at 450° C. for 15 min. A gas mixture containing about 75 mol % nitrogen and about 25 mol % air is fed to the reactor at a flow rate of 0.9 liter per min. During this time, temperature rise of about 50° C. is observed. The flow is maintained for 1 h. The content of the gas mixture is changed to about 50 mol % nitrogen and about 50 mol % air, and the calcination continues for another hour. Finally, the content of the gas mixture is changed to about 25 mol % nitrogen and about 75 mol % air, and the calcination continues for another hour. The catalyst bed is cooled to 200° C. under a nitrogen flow.

Steaming of Decoked Catalyst

Water is introduced to the catalyst bed at a rate of 25 mL per hour using a pump while a nitrogen flow rate is kept at about 0.9 liter per min. After steaming, the catalyst bed is purged with nitrogen at 350° C. for 2 h. The crushing strength of the regenerated magnesium oxide pellets on the top portion of the bed is measured (instrument: Chatillon, Model 150 L). An average value of crush strength measurements of 10 pellets is shown in Table 1.

Propylene Production Test

A catalyst mixture regenerated by the above method is crushed to mesh 18-30 and charged to a reactor (¾ inch in outside diameter and 16 inch in length) and tested for producing propylene under the same reaction condition as described above, except that the reaction temperature is maintained at 340 to 450° C. The test lasts for 5 h. The 2-butenes conversion and selectivity to propylene is shown in Table 1.

COMPARATIVE EXAMPLE 2

The procedure of Example 1 is repeated except that steaming step is omitted. The crushing strength of the regenerated magnesium oxide pellets on the top of the bed is 9 psig.

COMPARATIVE EXAMPLE 3

The Propylene Production Test procedure in Example 1 is repeated except that the catalyst bed consists of 7.5 g fresh MgO granules (mesh size 18-30, prepared by crushing fresh MgO pellets) at the top, and a mixture of 22.5 g fresh MgO granules and 7.5 g fresh $WO_3$/silica granules (mesh 18 to 30) at the bottom of the reactor. The 2-butenes conversion and selectivity to propylene is shown in Table 1.

The present invention produces a regenerated catalyst mixture containing MgO having the same crushing strength as the fresh MgO pellets. The regenerated catalyst mixture has nearly the same activity and selectivity as the fresh catalyst mixture. The invention reduces the attrition of the catalyst mixture, particularly the magnesium oxide without affecting its performance.

TABLE 1

| | Example | | |
|---|---|---|---|
| | 1 | C. 2 | C. 3 |
| Crushing strength of MgO | 15 | 9 | 15 |
| 2-Butenes conversion (%) | 55.0 | 56 | 57.9 |
| Propylene selectivity (%) | 91.6 | 92.0 | 92.1 |

I claim:

1. A method for regenerating a used catalyst mixture comprising the steps of:
   (a) decoking the used catalyst mixture in the presence of an oxygen-containing gas to produce a decoked catalyst mixture
   wherein the used catalyst mixture comprises:
      (i) an isomerization catalyst comprising magnesium oxide,
      (ii) a metathesis catalyst comprising an inorganic carrier and at least one of molybdenum oxide and tungsten oxide; and,
      (iii) coke and/or carbon deposits wherein the coke and/or carbon deposits are present in the pores of the used catalyst mixture or on the surface of the used catalyst mixture, and
   wherein the decoked catalyst mixture contains less than 0.5 wt % carbon; and
   (b) regenerating the decoked catalyst mixture by contacting the decoked catalyst mixture with steam at a temperature in the range of 100 to 300° C. to produce a regenerated catalyst mixture
   wherein the used catalyst mixture is recovered from a process for making propylene from a linear butene and ethylene.

2. The method of claim 1 wherein step (b) is performed at a temperature in the range of 150 to 250° C.

3. The method of claim 1 wherein isomerization catalyst comprises 95 wt% of magnesium oxide.

4. The method of claim 1 wherein metathesis catalyst comprises tungsten oxide.

5. The method of claim 4 wherein the inorganic carrier is silica.

6. The method of claim 1, wherein the oxygen containing gas further comprises a variable concentration of oxygen in the oxygen containing gas.

7. The method of claim 6, wherein the variable concentration of oxygen in the oxygen containing gas has a concentration that varies during the decoking process step.

8. The method of claim 7, wherein the catalyst mixture is in the presence of the oxygen containing gas for about three hours.

9. The method of claim 1, wherein the regenerated isomerization catalyst retains substantially the same crushing strength as a fresh isomerization catalyst.

* * * * *